United States Patent
Maturi

(10) Patent No.: US 11,400,080 B2
(45) Date of Patent: Aug. 2, 2022

(54) USE OF SIROLIMUS TO TREAT EXUDATIVE AGE-RELATED MACULAR DEGENERATION WITH PERSISTENT EDEMA

(71) Applicant: Santen Pharmaceutical Co., Ltd., Osaka (JP)

(72) Inventor: Raj K. Maturi, Indianapolis, IN (US)

(73) Assignee: Santen Pharmaceutical Co., Ltd., Osaka (JP)

(*) Notice: Subject to any disclaimer, the term of this patent is extended or adjusted under 35 U.S.C. 154(b) by 326 days.

(21) Appl. No.: 16/303,932

(22) PCT Filed: May 25, 2017

(86) PCT No.: PCT/JP2017/019551
§ 371 (c)(1),
(2) Date: Nov. 21, 2018

(87) PCT Pub. No.: WO2017/204298
PCT Pub. Date: Nov. 30, 2017

(65) Prior Publication Data
US 2020/0147056 A1   May 14, 2020

Related U.S. Application Data

(60) Provisional application No. 62/341,543, filed on May 25, 2016.

(51) Int. Cl.
| | |
|---|---|
| *A61K 31/436* | (2006.01) |
| *A61P 27/02* | (2006.01) |
| *A61K 9/00* | (2006.01) |
| *A61K 9/08* | (2006.01) |
| *A61K 31/7105* | (2006.01) |
| *A61K 45/06* | (2006.01) |

(52) U.S. Cl.
CPC .......... *A61K 31/436* (2013.01); *A61K 9/0019* (2013.01); *A61K 9/0048* (2013.01); *A61K 9/08* (2013.01); *A61K 31/7105* (2013.01); *A61P 27/02* (2018.01); *A61K 45/06* (2013.01)

(58) Field of Classification Search
None
See application file for complete search history.

(56) References Cited

U.S. PATENT DOCUMENTS

| | | |
|---|---|---|
| 5,387,589 A | 2/1995 | Kulkarni |
| 2006/0182771 A1 | 8/2006 | Dor |
| 2006/0257450 A1 | 11/2006 | Mudumba et al. |
| 2006/0258698 A1 | 11/2006 | Mudumba et al. |
| 2006/0264453 A1 | 11/2006 | Mudumba et al. |
| 2009/0074786 A1 | 3/2009 | Dor |
| 2010/0015158 A1 | 1/2010 | Robinson et al. |
| 2010/0227879 A1 | 9/2010 | Mudumba et al. |
| 2013/0197024 A1 | 8/2013 | Mudumba et al. |
| 2013/0295094 A1 | 11/2013 | Yancopoulos |
| 2014/0194461 A1 | 7/2014 | Mudumba et al. |
| 2014/0235678 A1 | 8/2014 | Bottger et al. |
| 2014/0322206 A1 | 10/2014 | Whitcup et al. |
| 2015/0150794 A1 | 6/2015 | Mudumba et al. |
| 2016/0101152 A1 | 4/2016 | Yancopoulos |
| 2016/0303093 A1 | 10/2016 | Mudumba et al. |
| 2017/0020809 A1 | 1/2017 | Mudumba et al. |
| 2017/0202911 A1 | 7/2017 | Yancopoulos |
| 2017/0266109 A1 | 9/2017 | Mudumba et al. |
| 2018/0311152 A1 | 11/2018 | Mudumba et al. |
| 2018/0339018 A1 | 11/2018 | Yancopoulos |
| 2019/0046609 A1 | 2/2019 | Yancopoulos |
| 2019/0247463 A1 | 8/2019 | Yancopoulos |
| 2019/0336441 A1 | 11/2019 | Whitcup et al. |
| 2021/0023173 A1 | 1/2021 | Yancopoulos |
| 2021/0085753 A1 | 3/2021 | Yancopoulos |
| 2021/0121524 A1 | 4/2021 | Yancopoulos |

FOREIGN PATENT DOCUMENTS

| | | |
|---|---|---|
| CN | 101137369 A | 3/2008 |
| CN | 101146536 A | 3/2008 |
| CN | 101827523 A | 9/2010 |
| CN | 102008437 A | 4/2011 |
| CN | 102159246 A | 8/2011 |
| JP | 2008-530127 A | 8/2008 |
| JP | 2014-503555 A | 2/2014 |
| JP | 2014-518232 A | 7/2014 |
| WO | 2000/009109 A2 | 2/2000 |

(Continued)

OTHER PUBLICATIONS

Stahl et al., "Rapamycin reduces VEGF expression in retinal pigment epithelium (RPE) and inhibits RPE-induced sprouting angiogenesis in vitro", FEBS Letters, vol. 582 (2008), pp. 3097-3102. (Year: 2008).*

International Preliminary Report on Patentability received for PCT Patent Application No. PCT/JP2017/019551, dated Dec. 6, 2018, 6 pages.

International Search Report and Written Opinion received for PCT Patent Application No. PCT/JP2017/019551, dated Aug. 8, 2017, 6 pages.

Jaffe et al., "Macular Morphology and Visual Acuity in the Comparison of Age-related Macular Degeneration Treatments Trials", Ophthalmology, vol. 120, No. 9, 2013, pp. 1860-1870.

Rein et al., "Forecasting Age-Related Macular Degeneration Through the Year 2050—The Potential Impact of New Treatments", Archives of Ophthalmology, vol. 127, No. 4, 2009, pp. 533-540.

(Continued)

*Primary Examiner* — Savitha M Rao
*Assistant Examiner* — Gregg Polansky
(74) *Attorney, Agent, or Firm* — Morrison & Foerster LLP

(57) ABSTRACT

This invention relates to a method for treatment of persistent edema in patients with exudative age-related macular degeneration. In particular, the present invention relates to treatment of wet age-related macular degeneration with intravitreal sirolimus in subjects that had an inadequate response to prior treatment with an intravitreal anti-vascular endothelial growth factor agent.

13 Claims, 6 Drawing Sheets

(56) References Cited

FOREIGN PATENT DOCUMENTS

| WO | 2004/027027 A2 | 4/2004 |
|---|---|---|
| WO | 2005/027906 A1 | 3/2005 |
| WO | 2006/086744 A1 | 8/2006 |
| WO | 2006/086750 A1 | 8/2006 |
| WO | 2006/102378 A2 | 9/2006 |
| WO | 2007/092620 A2 | 8/2007 |
| WO | 2007/112052 A2 | 10/2007 |
| WO | 2009/023877 A2 | 2/2009 |
| WO | 2010/129622 A1 | 11/2010 |

OTHER PUBLICATIONS

The CATT Research Group, "Ranibizumab and Bevacizumab for Neovascular Age-Related Macular Degeneration", The New England Journal of Medicine, vol. 364, No. 20, 2011, pp. 1897-1908.
Extended European Search Report issued in European Application No. 17802884.1, dated Jan. 9, 2020, 9 pages.
Nussenblatt et al. (2010). "A Randomized Pilot Study of Systemic Immunosuppression in the Treatment of Age-Related Macular Degeneration with Choroidal Neovascularization," Retina, 30(10): 1579-1587.
Stahl et al. (2008). "Rapamycin Reduces VEGF Expression in Retinal Pigment Epithelium (RPE) and Inhibits RPE-induced Sprouting Angiogenesis In Vitro" FEBS Letters, 582:3097-3102.
ClinicalTrials.gov Identifier NCT00766337 (2013) Phase 2 Study of an Ocular Sirolimus (Rapamycin) Formulation in Combination with Lucentis in Patients With Age-Related Macular Degeneration (EMERALD), available online at <https://clinicaltrials.gov/ct2/show/record/NCT00766337>, 12 pages.
Dugel, (2009). "Sirolimus in the Treatment of Retinal Diseases, mTOR inhibitors: A new class of therapeutics," Retina Today, pp. 38-41.
Ishikawa et al., (2015). "Future Therapies of Wet Age-Related Macular Degeneration," Journal of Ophthalmology, 2015:138070, 10 pages.
Office Action received for EP Patent Application No. 17802884.1, dated Aug. 20, 2020, 4 pages.
Office Action received for RU Patent Application No. 2018145017, dated Aug. 26, 2020, 18 pages. (8 pages of English translation and 10 pages of Russian document).
Ohr et al., (2012). "Aflibercept in wet age-related macular degeneration: a perspective review," Ther Adv Chronic Dis, 3(4)153-161.
Takeda et al., (2007). "Pegaptanib and ranibizumab for neovascular age-related macular degeneration: a synthetic review," Br J Ophthalmol., 91:1177-1182.
Ting et al., (2002). "Decreased Visual Acuity Associated With Cystoid Macular Edema in Neovascular Age-related Macular Degeneration," Arch Ophthalmol., 120:731-737.
Office Action received for JP Patent Application No. 2018-561748 dated Apr. 6, 2021, 10 pages. (6 pages of English Translation + 4 pages of Official Copy).
Blumenkranz, (May 2007). "Sirolimus and mTOR Inhibition in Ocular Disease: An Update," Retina Today, 2 pages.
Office Action received for CN Patent Application No. 201780032353.1, dated Mar. 29, 2021, 13 pages (7 pages of English translation and 6 pages of Chinese document.
Notice of Allowance received for Japanese Patent Application No. 2018-561748 dated Aug. 31, 2021, 5 pages. (3 pages of English Translation and 2 pages of Official Copy).
Office Action for Korean Application No. 10-2018-7037333, dated Jun. 23, 2021, English translation plus Korean language document. 10 pages.
Office Action received for Japanese Patent Application No. 2018-561748 dated Jul. 13, 2021, 4 pages. (2 pages of English Translation and 2 pages of Official Copy).

\* cited by examiner

USE OF SIROLIMUS TO TREAT EXUDATIVE AGE-RELATED MACULAR DEGENERATION WITH PERSISTENT EDEMA

CROSS REFERENCE TO RELATED APPLICATIONS

This application is a U.S. National Phase patent application of International Application No. PCT/JP2017/019551, filed May 25, 2017, which claims priority to U.S. Provisional Application No. 62/341,543, filed May 25, 2016, each of which is hereby incorporated by reference in in its entirety.

TECHNICAL FIELD

This invention relates to a method for treatment of persistent edema in patients with exudative age-related macular degeneration. In particular, the present invention relates to treatment of wet age-related macular degeneration with intravitreal sirolimus in subjects that had an inadequate response to prior treatment with an intravitreal anti-vascular endothelial growth factor agent.

BACKGROUND ART

Age-related macular degeneration (AMD) is the leading cause of severe vision loss in people over the age of 65 in the United States (Rein et al., Arch Ophthalmology, 127: 533-540, 2009). The majority of severe vision loss due to advanced AMD is related to the onset of choroidal neovascularization (CNV). Neovascular AMD (wet AMD) is characterized by the growth of choroidal vessels into the subretinal space. These vessels have a tendency to leak fluid and blood, causing retinal edema and central vision loss.

The Comparison of Age-related Macular Degeneration Treatments Trials: LUCENTIS (Trade Mark)-AVASTIN (Trade Mark) Trial (CATT) data demonstrated that it is difficult to achieve anatomic flattening of the macula in patients with neovascular AMD (NCT00593450). In brief, CATT compared the effect of two anti-vascular endothelial growth factor (VEGF) treatments, ranibizumab and bevacizumab. After one year of required monthly treatment in both the bevacizumab and ranibizumab groups, approximately 50% of subjects continued to have intraretinal and/or subretinal fluid on optical coherence tomography (CATT Research Group, New Engl J Med, 364:1897-1908, 2011). When fluid remains present in these structures, retreatment is typically necessary to stabilize vision. Moreover, subjects with persistent intraretinal fluid generally have poorer visual gains as a consequence of anti-VEGF treatment (Jaffe et al., Ophthalmology, 120:1860-1870, 2013).

Thus, there remains a need in the art for treatment regimens and medicaments to reduce intraretinal edema in subjects with neovascular AMD.

CITATION LIST

Non Patent Literature

NPL 1: Rein et al., Arch Ophthalmology, 127:533-540, 2009
NPL 2: CATT Research Group, New Engl J Med, 364:1897-1908, 2011
NPL 3: Jaffe et al., Ophthalmology, 120:1860-1870, 2013

SUMMARY OF INVENTION

This invention relates to a method for treatment of persistent edema in patients with exudative age-related macular degeneration. In particular, the present invention relates to treatment of wet age-related macular degeneration with intravitreal sirolimus in subjects that had an inadequate response to prior treatment with an intravitreal anti-vascular endothelial growth factor agent.

The present invention provides methods of treating exudative age-related macular degeneration (AMD) in a human subject, the method comprising: administering an effective amount of a liquid formulation to the human subject by intravitreal injection to treat exudative AMD, wherein the liquid formulation comprises from about 1% (w/w) to about 10% sirolimus or a pharmaceutically acceptable salt thereof; and the human subject has persistent intraretinal or subretinal edema due to exudative AMD despite previous intravitreal anti-vascular endothelial growth factor (VEGF) treatment. In some embodiments, the effective amount of the liquid formulation comprises from 200 to 900 μg sirolimus, or from 400 to 480 μg sirolimus. In some embodiments, the previous intravitreal anti-VEGF treatment comprises at least three previous injections in the past three to seven months, or in the past five months. In some embodiments, the anti-VEGF treatment comprises treatment with an anti-VEGF monoclonal antibody or VEGF-binding fragment thereof. In some of these embodiments, the anti-VEGF monoclonal antibody is a human antibody or a humanized antibody. In some embodiments, the anti-VEGF treatment comprises one or more of the group consisting of bevacizumab, ranibizumab, aflibercept, pegaptanib, and combinations thereof. In some embodiments, the subject is 50 years of age or older. In some of these embodiments, the subject is from 50 to 64 years of age, from 65 to 74 years of age, or 75 years of age or older. In some embodiments, the treatment of exudative AMD achieves a decrease in edema in a treated eye of at least about −15 microns in central subfield thickness as measured by optical coherence tomography about one month (±week) after administration of the liquid formulation. In some preferred embodiments, the administering is done once very two months for at least two months and the treatment of exudative AMD achieves a decrease in edema in a treated eye of at least about −30 microns in central subfield thickness as measured by optical coherence tomography about one month (±week) after a second administration of the liquid formulation. In some embodiments, the administering is done once very two months for at least four months and the treatment of exudative AMD achieves a decrease in edema in a treated eye of at least about −40 microns in central subfield thickness as measured by optical coherence tomography about one month (±week) after a third administration of the liquid formulation. In some embodiments, visual acuity of the treated eye remains stable or improves by about one month (±week) after administration of the liquid formulation. In some embodiments, the treatment of exudative AMD achieves a reduction in subretinal retinal hyper-reflective material in a treated eye. In some embodiments, the treatment of exudative AMD achieves a reduction in serous pigment epithelial detachment thickness in a treated eye. In some preferred embodiments, the liquid formulation comprises about 2% (w/w) sirolimus or a pharmaceutically acceptable salt thereof, about 94% (w/w) polyethylene glycol 400, and about 4% (w/w) ethanol and the effective amount of the liquid formulation comprises about 440 μg sirolimus.

In addition, the present invention provides methods of treating exudative age-related macular degeneration (AMD) in a human subject, the method comprising: administering an effective amount of a liquid formulation to the human subject by intravitreal injection to treat exudative AMD; and administering an effective amount of an anti-VEGF agent to the human subject by intravitreal injection to treat the exudative AMD, wherein the liquid formulation comprises from about 1% (w/w) to about 10% sirolimus or a pharmaceutically acceptable salt thereof, the human subject has persistent intraretinal or subretinal edema due to exudative AMD despite previous intravitreal anti-vascular endothelial growth factor (VEGF) treatment, and the anti-VEGF agent is administered at from one to five weeks after administration of the liquid formulation. In some embodiments, the effective amount of the liquid formulation comprises from 200 to 900 µg sirolimus or from 400 to 480 µg sirolimus. In some embodiments, the previous intravitreal anti-VEGF treatment comprises at least three previous injections in the past three to seven months. In some embodiments, the anti-VEGF agent comprises an anti-VEGF monoclonal antibody or VEGF-binding fragment thereof. In some embodiments, the anti-VEGF monoclonal antibody is a human antibody or a humanized antibody. In some embodiments, the anti-VEGF agent comprises bevacizumab, ranibizumab, aflibercept, pegaptanib, or combinations thereof. In some embodiments, the subject is 50 years of age or older. In some embodiments, the subject is from 50 to 64 years of age, from 65 to 74 years of age, or 75 years of age or older. In some embodiments, the treatment of exudative AMD achieves a decrease in edema in a treated eye of at least about −15 microns in central subfield thickness as measured by optical coherence tomography about one month (±week) after administration of the liquid formulation. In some embodiments, the treatment of exudative AMD achieves a decrease in edema in a treated eye of at least about −45 microns in central subfield thickness as measured by optical coherence tomography about one month (±week) after administration of the anti-VEGF agent. In some embodiments, visual acuity of the treated eye remains stable or improves by about one month (±week) after administration of the liquid formulation. In some embodiments, visual acuity of the treated eye remains stable or improves by about one month (±week) after administration of the anti-VEGF agent. In some embodiments, the treatment of exudative AMD achieves a reduction in subretinal retinal hyper-reflective material in a treated eye. In some embodiments, the treatment of exudative AMD achieves a reduction in serous pigment epithelial detachment thickness in a treated eye. In some preferred embodiments, the liquid formulation comprises about 2% (w/w) sirolimus or a pharmaceutically acceptable salt thereof, about 94% (w/w) polyethylene glycol 400, and about 4% (w/w) ethanol and the effective amount of the liquid formulation comprises about 440 µg sirolimus. In some preferred embodiments, both the liquid formulation and the anti-VEGF agent are administered at least twice, wherein the anti-VEGF agent is administered every seven to nine weeks, and the liquid formulation is administered every three to five weeks after administration of the anti-VEGF agent. In some embodiments, both the liquid formulation and the anti-VEGF agent are administered at least three times.

DESCRIPTION OF EMBODIMENTS

Figure 1:
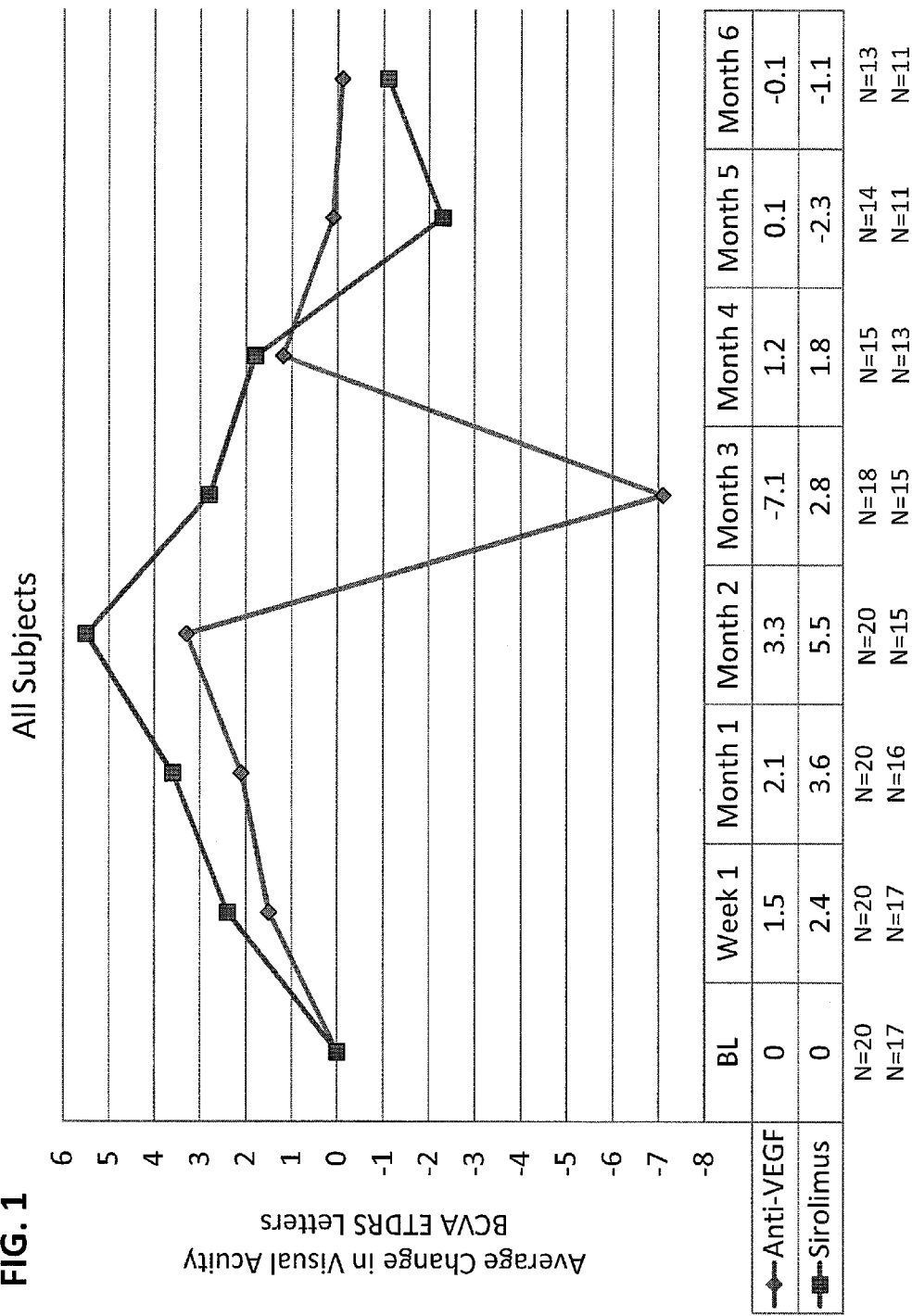
FIG. 1 shows the average change in visual acuity in subjects of the sirolimus and anti-VEGF treatment groups as determined by measuring best corrected visual acuity (BCVA).

This invention relates to a method for treatment of persistent edema in patients with exudative age-related macular degeneration. In particular, the present invention relates to treatment of wet age-related macular degeneration with intravitreal sirolimus in subjects that had an inadequate response to prior treatment with an intravitreal anti-vascular endothelial growth factor agent. As described in Example 1, there was a measurable anatomic improvement when subjects with persistent edema despite previous anti-VEGF treatment were treated with intravitreal sirolimus (rapamycin). Additionally, as described in Example 2, there was an improvement in visual acuity when subjects with persistent edema despite previous anti-VEGF treatment were treated with both intravitreal sirolimus (rapamycin) and an intravitreal anti-VEGF agent.

Specifically, the present disclosure provides a method of treating exudative age-related macular degeneration (AMD or ARMD) in a human subject, comprising:

administering an effective amount of a liquid formulation to the human subject by intravitreal injection to treat exudative AMD, wherein the liquid formulation comprises from about 1% (w/w) to about 10% sirolimus or a pharmaceutically acceptable salt thereof; and the human subject has persistent intraretinal or subretinal edema due to exudative AMD despite previous intravitreal anti-vascular endothelial growth factor (VEGF) treatment. Exudative AMD, is also known as neovascular AMD and wet AMD, involves active choroidal neovascularization. CNV can be identified when leakage or increased stippling is observed on fluorescein angiography and when fluid (edema) is detected on optical coherence tomography (OCT). In some embodiments, the methods further comprise:

administering an effective amount of an anti-VEGF agent to the human subject by intravitreal injection to treat the exudative AMD, wherein the anti-VEGF agent is administered at from one to five weeks after administration of the liquid formulation.

In some embodiments, the effective amount of the liquid formulation comprises a dose of from about 200 µg to about 900 µg sirolimus. That is the effective amount of sirolimus is: greater than about (lower limit) 200, 300, 400, 500, 600, 700 or 800 µg; and less than about (upper limit) 900, 800, 700, 600, 500, 400, or 300 µg; provided that the lower limit is less than the upper limit.

The liquid formulation of the present disclosure comprises from about 1% (w/w) to about 10% (w/w) sirolimus or a pharmaceutically acceptable salt thereof. That is the liquid formulation comprises: greater than about (lower limit) 1.0, 1.5, 2.0, 2.5, 3.0, 3.5, 4.0, 4.5, 5.0, 5.5, 6.0, 6.5, 7.0, 7.5, 8.0, 8.5 or 9% sirolimus; and less than about (upper limit) 10, 9.5, 9.0, 8.5, 8.0, 7.5, 7.0, 6.5, 6.0, 5.5, 5.0, 4.5, 4.0, 3.5, 3.0, 2.5, or 2.0% sirolimus; provided that the lower limit is less than the upper limit.

In preferred embodiments, the liquid formulation is a liquid solution in which sirolimus is dissolved in a solvent. An exemplary solvent is polyethylene glycol (e.g., PEG 400), which may further comprise ethanol. In any event, the liquid formulation is sterile and preferably provided in a single use container (e.g., vial or syringe).

The methods of the present disclosure are effective in achieving a decrease in edema from baseline in a treated eye that is measurable by OCT. In some embodiments, the decrease in edema is from about −15 microns to about −105 microns. That is, the decrease in edema is: greater than about (lower limit) −15, −30, −45, −60, −75, or −90 microns; and less than about (upper limit) −105, −90, −75, −60, −45, or −30 microns; provided that the lower limit is less than the upper limit. In some embodiments, the decrease in edema is determined from one week to five weeks after administration of an effective amount of a liquid formulation comprising sirolimus. In some embodiments, more than one dose (e.g., n+1) of the liquid formulation is administered over a period of time. In such embodiments, the decrease in edema is determined from one week to five weeks after administration of the first dose, the second dose and/or the further dose if any. In some preferred embodiments, the decrease in edema is determined from three to five weeks after administration of at least one dose of the liquid formulation.

Definitions

As used herein and in the appended claims, the singular forms "a," "an," and "the" include plural references unless indicated otherwise. For example, "an" excipient includes one or more excipients.

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments. It is understood that aspects and embodiments described herein as "comprising" include "consisting of" and "consisting essentially of" embodiments.

The term "about" as used herein in reference to a value, encompasses from 90% to 110% of that value (e.g., about 20 µl of a liquid formulation refers to a value of from 18 µl to 22 µl of the liquid formulation).

The terms "individual" and "subject" refer to mammals, preferably humans.

The term "anti-VEGF agent" refers to a compound capable of blocking a biological activity of VEGF. In some embodiments, the anti-VEGF agent is an anti-VEGF monoclonal antibody such as bevacizumab (marketed as AVASTIN (Trade Mark) by Genentech, Inc., South San Francisco, Calif.) or ranibizumab (marketed as LUCENTIS (Trade Mark) by Genentech, Inc., South San Francisco, Calif.). In some embodiments, the anti-VEGF agent is a pegylated anti-VEGF aptamer such as pegaptanib (MACUGEN (Trade Mark) marketed by Eyetech Inc., Palm Beach Gardens, Fla.). In some embodiments, the anti-VEGF agent is a recombinant VEGF receptor such as aflibercept (marketed as EYLEA (Trade Mark) by Regeneron Pharmaceuticals, Inc., Tarrytown, N.J.).

The term "intravitreal VEGF treatment" refers to administration of a VEGF inhibitor to the vitreous of an eye of a subject in an effort to alleviate a sign or symptom of an ocular disease (e.g., exudative age-related macular degeneration). VEGF inhibitors that can be administered by intravitreal injection include but are not limited to ranibizumab, bevacizumab, aflibercept, pegaptanib, bevasiranib, siRNA-027 and ALN-VPS02 (see, e.g., Amadio et al., Pharm Res, 103:253,269, 2016).

An "effective amount" of an agent (e.g., sirolimus) disclosed herein is an amount sufficient to carry out a specifically stated purpose. An "effective amount" may be determined empirically in relation to the stated purpose. An "effective amount" or an "amount sufficient" of an agent is that amount adequate to affect a desired biological effect, such as a beneficial result, including a beneficial clinical result. The term "effective amount" in reference to a method of treatment refers to an amount of an agent effective to "treat" a disease or disorder in a subject (e.g., a mammal such as a human). An "effective amount" or an "amount sufficient" of an agent may be administered in one or more doses.

The terms "treating" or "treatment" of a disease refer to executing a protocol, which may include administering one or more drugs to an individual (human or other mammal), in an effort to alleviate a sign or symptom of the disease. Thus, "treating" or "treatment" does not require complete alleviation of signs or symptoms, does not require a cure, and specifically includes protocols that have only a palliative effect on the individual. As used herein, and as well-understood in the art, "treatment" is an approach for obtaining beneficial or desired results, including clinical results. Beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Palliating" a disease or disorder means that the extent and/or undesirable clinical manifestations of the disease or disorder are lessened and/or time course of progression of the disease or disorder is slowed, as compared to the expected untreated outcome. Further, palliation and treatment do not necessarily occur by administration of one dose, but often occur upon administration of a series of doses.

As used herein, the phrase "visual acuity of the treated eye remains stable" refers to a visual acuity that remains ±2 BCVA ETDRS letters of the baseline value (pre-treatment) by about one month (±week) after administration of the liquid formulation. As used herein, the phrase "visual acuity of the treated eye improves" refers to a visual acuity that increases by greater than 2 BCVA ETDRS letters of the baseline value (pre-treatment) by about one month (±week) after administration of the liquid formulation.

EXAMPLES

Abbreviations: AMD (age-related macular degeneration); BCVA (best corrected visual acuity); BL (baseline); CNV (choroidal neovascularization); CST (central subfield thickening); ETDRS (early treatment diabetic retinopathy study); EYL (EYLEA (Trade Mark), aflibercept for intravitreal injection marketed by Regeneron Pharmaceuticals, Inc., Tarrytown, N.Y.); IOP (intraocular pressure); IVT (intravitreal); OCT (optical coherence tomography); SRL (sirolimus); Tx (treatment) and VEGF (vascular endothelial growth factor).

Although the foregoing disclosure has been described in some detail by way of illustration and example for purposes of clarity and understanding, it will be apparent to those skilled in the art that certain changes and modifications may be practiced. Therefore, descriptions and examples should not be construed as limiting the scope of the disclosure.

Example 1

Sirolimus Versus Anti-VEGF For Treatment of Exudative AMD

This study was done to determine safety and efficacy of intravitreal injection of sirolimus (rapamycin) in subjects with exudative AMD with persistent intraretinal or subretinal edema despite previous intravitreal anti-VEGF treatment. This study was a single-center, randomized, subject-masked trial over the course of six months with eight scheduled visits.

Study Population. Thirty human patients, who were 50 years of age or older at baseline were recruited according to the following inclusion and exclusion criteria. If both eyes met all of the inclusion/exclusion criteria the eye with the worse BCVA at baseline was selected as the study eye. If both eyes met all of the inclusion/exclusion criteria and BCVA values were identical for both eyes, the right eye was selected as the study eye.

Ocular Inclusion Criteria:
 (i) BCVA of 5-65 (20/800-20/50), inclusive, in study eye;
 (ii) presence of choroidal neovascularization secondary to AMD;
 (iii) persistent edema despite at least three previous intravitreal anti-VEGF injections in the past five months;
 (iv) deferred injection of anti-VEGF for at least four weeks not contraindicated; and
 (v) clear ocular media and adequate pupil dilation to permit good quality photographic imaging.

Ocular Exclusion Criteria:
 (i) greater than 100 micron decrease in central subfield thickness as measured by OCT since the last intravitreal anti-VEGF injection in the study eye;
 (ii) aphakia;
 (iii) history of pars plana vitrectomy in the study eye;
 (iv) history of major ophthalmic surgery in the study eye in the past three months and any ophthalmic surgery in the study eye within the past 30 days;
 (v) history of significant ocular disease or condition other than exudative AMD that may confound results;
 (vi) uncontrolled glaucoma (intraocular pressure >21 mm Hg despite treatment with ocular hypotensive medications at baseline);
 (vii) absence of active ocular or periocular infections, or malignancy; and
 (viii) presence of significant epiretinal membrane.

Treatments. Systemic anti-VEGF medications were prohibited. Therapies for the non-study eye were permissible at any time.

Study Treatment (Group 1). Intravitreal injection of 440 μg sirolimus (Santee Inc., Emeryville, Calif.) given at baseline, month 2 and month 4. In brief, 20 μl of a liquid solution containing 2% (w/w) sirolimus 94% (w/w) polyethylene glycol 400, and 4% (w/w) ethanol given. Sham intravitreal injection given at month 1, month 3 and month 5.

Comparator Treatment (Group 2). Intravitreal injection of anti-VEGF per patient/investigator choice (pegaptanib, aflibercept, bevacizumab or ranibizumab) given at baseline and thereafter monthly per clinical criteria. Sham intravitreal injections given when retreatment criterion was not met at month 1 or any later visit.

Administration. Pre-injection antibiotic eye drops were permitted. An inferior temporal intravitreal injection site was recommended, subject to the physician's discretion. The injection needle was to be inserted 3.5-4.0 mm posterior to the limbus aiming towards the center of the globe, avoiding the horizontal meridian to avoid injection into the visual axis. A different scleral site was to be used with each subsequent injection. If performing a sham injection, the tip of the syringe (without a needle or medication) was to be pressed gently against the conjunctiva. Both intraocular pressure and the perfusion of the optic nerve head were monitored and managed appropriately after injection. Post-injection antibiotic eye drops were permitted.

Table 1-1 sets out the schedule for ophthalmic procedures. Subjects were given a ±1 week window for each monthly visit. Unless otherwise indicated the procedures were done on both the treated and untreated eyes.

TABLE 1-1

Ophthalmic Procedure Schedule

| Procedure | Base | week 1 | month 1 | month 2 | month 3 | month 4 | month 3 | month 6 |
|---|---|---|---|---|---|---|---|---|
| BCVA | x | x | x | x | x | x | x | x |
| IOP | x | x | x | x | x | x | x | x |
| Bimicroscopy | x | x | x | x | x | x | x | x |
| Indirect Ophthalmoscopy | x | x | x | x | x | x | x | x |
| Heidelberg OCT | x | x | x | x | x | x | x | x |
| FA, autofluor, fundus photos | x | | | | | | | x |
| Sirolimus or sham Group 1[a] | x | | sham | x | sham | x | sham | |
| Anti-VEGF Group 2[b] | x | | x | x | x | x | x | |

[a]Group 1 received an injection of sirolimus at Baseline, Month 2, and Month 4. Group 1 received a sham injection at Month 1, Month 3, and Month 5.
[b]Group 2 received anti-VEGF at baseline and monthly when clinical retreatment criteria were met. Group 2 received a sham injection at any monthly visit that retreatment criterion were not met.

Retreatment Criteria. Subjects in both treatment groups received retreatment monthly as long as continued subretinal edema, intraretinal edema or active CNV was present.

Baseline Visit. The following procedures were performed:
 standard BCVA, using ETDRS method following refraction;
 complete ophthalmic examination including slit-lamp biomicroscopy, indirect ophthalmoscopy and TOP;
 Heidelberg OCT imaging:
 dilated color fundus photography;
 Heidelberg autofluorescence imaging;
 Heidelberg fluorescein angiography; and
 perform assigned intravitreal injection.

Figure 2:
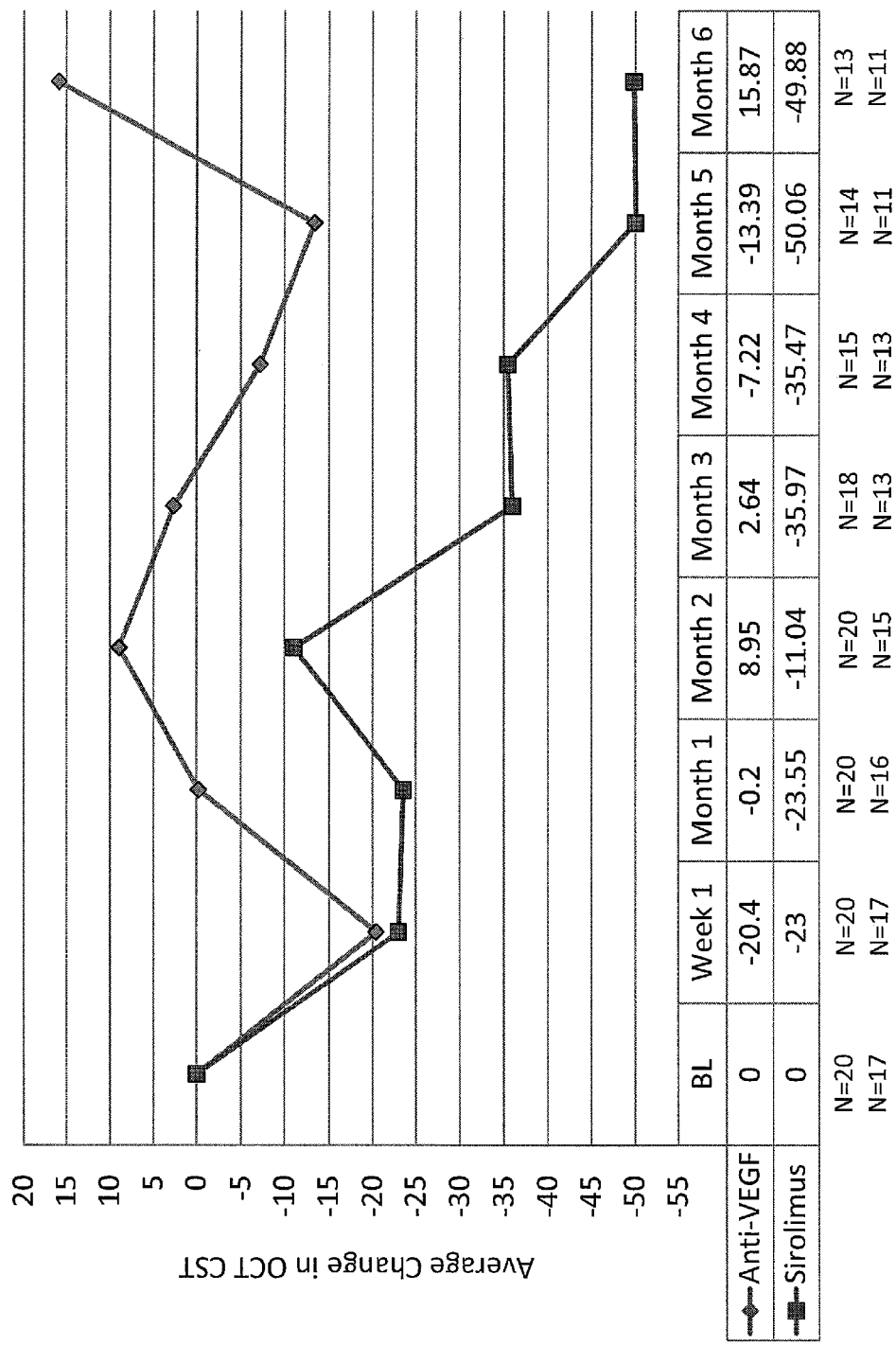
FIG. 2 shows the average change in central subfield thickness (CST) in subjects of the sirolimus and anti-VEGF treatment groups as determined by optical coherence tomography (OCT).
Figure 3:
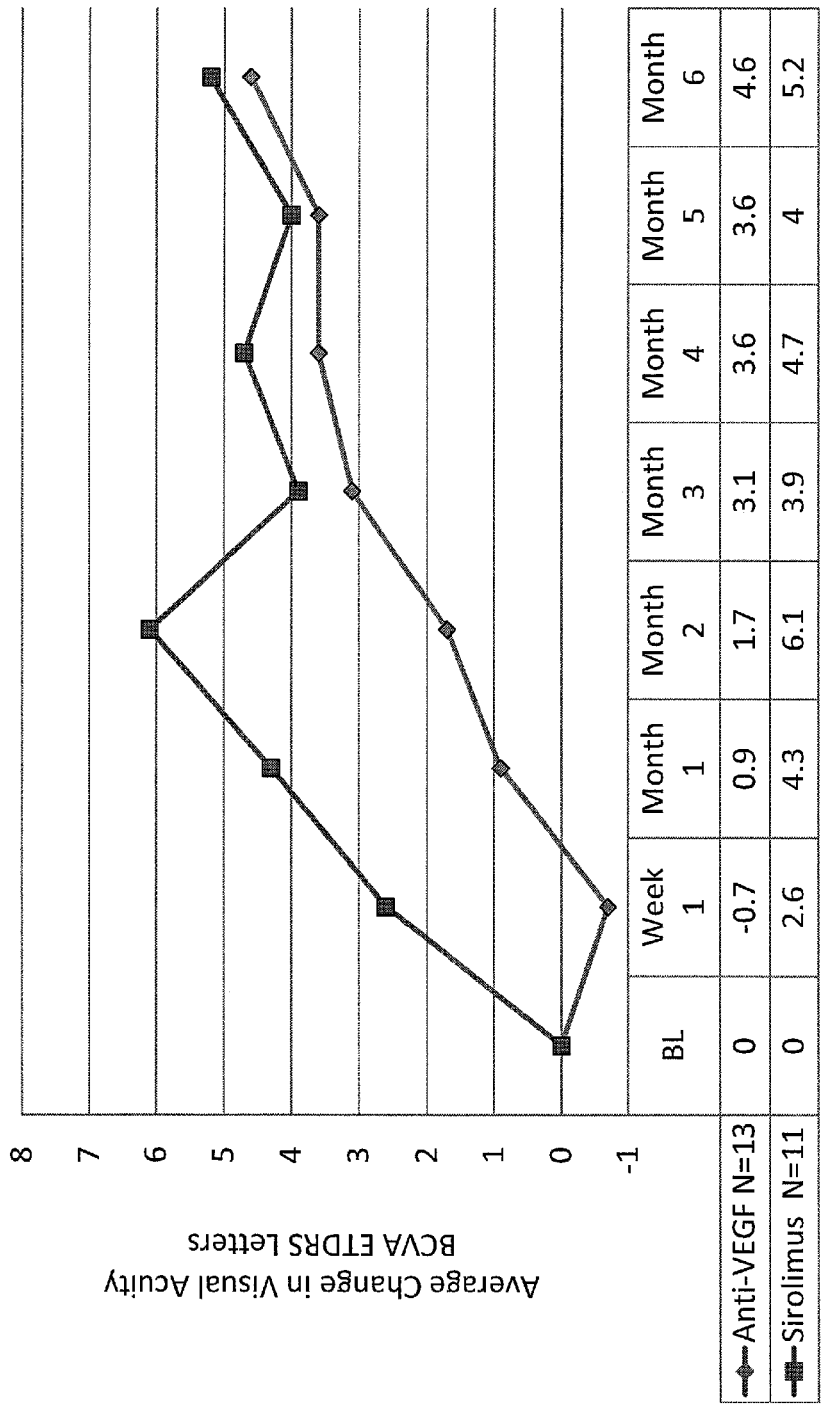
FIG. 3 shows the average change in visual acuity in subjects of the sirolimus and anti-VEGF treatment groups as determined by measuring best corrected visual acuity (BCVA) upon completion of the study of Example 1.
Figure 4:
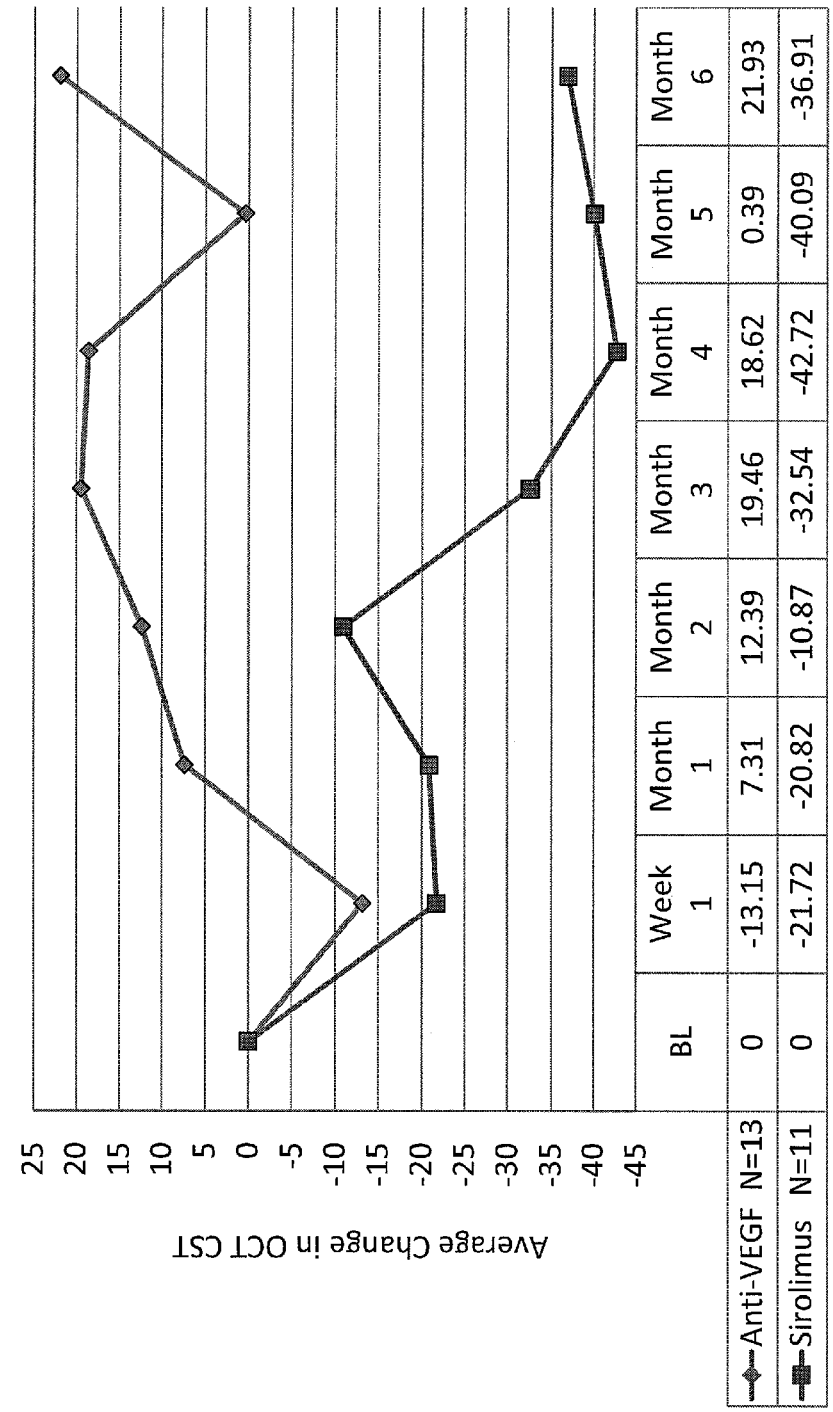
FIG. 4 shows the average change in central subfield thickness (CST) in subjects of the sirolimus and anti-VEGF treatment groups as determined by optical coherence tomography (OCT) upon completion of the study of Example 1.

Week 1 Visit included queries for adverse events, medication changes and medical procedures. The following procedures were performed:

standard BCVA, using ETDRS method following refraction;
complete ophthalmic examination including slit-lamp biomicroscopy, indirect ophthalmoscopy and TOP;
Heidelberg OCT imaging;
Month 1, 2, 3, 4 and 5 Visits included queries for adverse events, medication changes and medical procedures. The following procedures were performed:
standard BCVA, using ETDRS method following refraction;
complete ophthalmic examination including slit-lamp biomicroscopy, indirect ophthalmoscopy and TOP;
Heidelberg OCT imaging; and
perform assigned intravitreal injection per protocol (or sham).
Month 6 (exit) Visit included queries for adverse events, medication changes and medical procedures. The following procedures were performed:
standard BCVA, using ETDRS method following refraction;
complete ophthalmic examination including slit-lamp biomicroscopy, indirect ophthalmoscopy and TOP;
Heidelberg OCT imaging;
dilated color fundus photography;
Heidelberg autofluorescence imaging; and
Heidelberg fluorescein angiography.
The primary efficacy endpoint includes change in edema from baseline to month 6 as measured by CST on Heidelberg OCT.
Secondary efficacy endpoints include:
change in BCVA from baseline to month 6;
change in intraretinal and subretinal edema from baseline to month 6;
change in CNV lesions components including subretinal retinal hyper-reflective material (SRHM) and serous pigment epithelial detachment (PED) thickness;
number of subjects rescued to standard of care treatment in Group 1; and
number of injections required to control extravasation CNV based on volume of subretinal fluid.
Data Analysis. The analysis of data from the study is performed when all subjects have either completed the visit at Month 6 or discontinued early from the study. Both univariate and multivariate analyses are done.
Continuous variables will be summarized with means and standard deviations and medians with min and max values and categorical variables with frequencies and percentages. Standard parameters and statistical tests will be performed to evaluate for the primary and secondary end points. Specifically, mean change in the CST, manual determination for the presence of subretinal fluid and intraretinal fluid in each group at month six (and at other time points), change in BCVA between baseline and month six, and the number of anti-VEGF injections needed in each group will be measured.
Results. As shown in FIG. 2 and FIG. 4, the study was successful in achieving the primary endpoint of reducing edema from baseline to month 6 in subjects of Group 1, who were treated with intravitreal sirolimus after previously having been treated with intravitreal anti-VEGF. In particular, subjects in Group 1 having completed the study through month 6 had an average reduction in edema from baseline to months 3-6 (2 sirolimus treatments) of from about −30 to −40. In contrast, subjects in Group 2 having completed the study through month 6 had an average increase in edema from baseline to months 3-6 (up to 4, 5 or 6 anti-VEGF treatments) of from about 0 to about +20. Additionally, as shown in FIG. 1 and FIG. 3, the average change in visual acuity in the subjects of Group 1 was comparable to that of Group 2 from baseline to months 3-6. Thus, subjects with exudative AMD with persistent intraretinal or subretinal edema due to neovascular AMD despite previous intravitreal Anti-VEGF treatment clearly receive benefit from treatment with intravitreal sirolimus.

Example 2

Sirolimus Plus Anti-VEGF Versus Anti-VEGF Alone for Treatment of Exudative AMD

This study was done to determine safety and efficacy of intravitreal injection of sirolimus (rapamycin) with adjunct anti-VEGF in subjects with persistent edema due to neovascular AMD versus anti-VEGF treatment alone. This study was a single-center, randomized, subject-masked trial over the course of six months with eleven scheduled visits.

Study Population. Twenty human patients, who were 50 years of age or older at baseline were recruited according to the following inclusion and exclusion criteria. If both eyes met all of the inclusion/exclusion criteria the eye with the best potential for visual improvement (worse BCVA) at baseline was selected as the study eye. If both eyes met all of the inclusion/exclusion criteria and BCVA values were identical for both eyes, the right eye was selected as the study eye.

Ocular Inclusion Criteria:
(i) BCVA of 5-75 (20/800-20/30), inclusive, in study eye;
(ii) presence of choroidal neovascularization secondary to AMD;
(iii) at least three previous intravitreal anti-VEGF injections in the past five months;
(iv) deferred injection of anti-VEGF for at least four weeks not contraindicated; and
(v) clear ocular media and adequate pupil dilation to permit good quality photographic imaging.

Ocular Exclusion Criteria:
(i) greater than 100 micron decrease in central subfield thickness as measured by OCT since the last standard of care visit;
(ii) aphakia;
(iii) history of pars plana vitrectomy in the study eye;
(iv) history of major ophthalmic surgery in the study eye in the past three months and any ophthalmic surgery in the study eye within the past 30 days;
(v) history of significant ocular disease or condition other than exudative AMD that may confound results;
(vi) uncontrolled glaucoma (intraocular pressure >21 mm Hg despite treatment with ocular hypotensive medications at baseline);
(vii) absence of active ocular or periocular infections, or malignancy; and
(viii) presence of significant epiretinal membrane.

Treatments. Systemic anti-VEGF medications were prohibited. Therapies for the non-study eye were permissible at any time.

Study Treatment (Group 1). Intravitreal injection of SRL (sirolimus) given at baseline, and weeks 4, 12, 30, 28. Intravitreal injections of EYL (aflibercept) given at weeks 1, 8, 16, 24 and 32. At weeks 24 and 32, EYL injections were deferred if visual acuity score had not decreased by more than five letters and OCT CST had not increased by more than 50 microns since the last visit.

Comparator Treatment (Group 2). Intravitreal injection of EYL (aflibercept) given at baseline and weeks 8, 16, 24 and 32. Sham intravitreal injections given at weeks 1, 4, 12, 20 and 28 in order to maintain masking of patient to treatment assignment.

SRL injection: 20 µl of a liquid solution containing 2% (w/w) sirolimus 94% (w/w) polyethylene glycol 400, and 4% (w/w) ethanol. Each dose contained 440 µg sirolimus. The sirolimus solution was obtained from Santen Inc. (Emeryville, Calif.).

EYL injection: 50 µl of a liquid solution containing aflibercept (40 mg/ml), 10 mM sodium phosphate, 40 mM sodium chloride, 0.03% polysorbate 20, and 5% sucrose. Each dose contained 2 mg aflibercept. The aflibercept solution was obtained from Regeneron Pharmaceuticals, Inc. (Tarrytown, N.Y.).

Administration. Pre-injection antibiotic eye drops were permitted. An inferior temporal intravitreal injection site was recommended, subject to the physician's discretion. The injection needle was inserted 3.5-4.0 mm posterior to the limbus aiming towards the center of the globe, avoiding the horizontal meridian to avoid injection into the visual axis. A different scleral site was used with each subsequent injection. If performing a sham injection, the tip of the syringe (without a needle or medication) was pressed gently against the conjunctiva. Both intraocular pressure and the perfusion of the optic nerve head were monitored and managed appropriately after injection. Post-injection antibiotic eye drops were permitted.

Table 2-1 sets out the schedule for ophthalmic procedures. Subjects were given a ±1 week window for each visit. Abbreviations: * (study eye only); and sh (sham injection).

TABLE 2-1

Ophthalmic Procedure Schedule

| Week/Procedure | 0 | 1 | 4 | 8 | 12 | 16 | 20 | 24 | 28 | 32 | 36 |
|---|---|---|---|---|---|---|---|---|---|---|---|
| BCVA | x | x | x | x | x | x | x | x | x | x | x |
| IOP | x | x | x | x | x | x | x | x | x | x | x |
| Biomicroscopy | x | x* | x | x | x | x | x | x | x | x | x |
| Indirect Ophthalmoscopy | x | x* | x | x | x | x | x | x | x | x | x |
| Heidelberg OCT | x | x* | x | x | x | x | x | x | x | x | x |
| FA and fundus photos | x | | | | | | | | | | |
| SRL(S) and EYL(E) | S | E | S | E | S | E | S | E | S | E | |
| EYL(E) alone | E | sh | sh | E | sh | E | sh | E | sh | E | |

Retreatment Criteria: Subjects in both groups received retreatment (or sham) at each scheduled visit as long as continued subretinal edema, intraretinal edema or active choroidal neovascularization was present.

Rescue Criteria:
(i) subjects in the study group with a 10 letter decrease at two consecutive visits or a 15 letter decrease at any visit escaped to standard of care;
(ii) central retinal thickness increase by 50 microns or more associated with a 5 letter decrease escaped to standard of care; and
(iii) presence of new hemorrhage, worsening hemorrhage, new extra foveal fluid, or at the discretion of the investigator escape to standard of care.

Baseline Visit. The following procedures were performed:
standard BCVA, using ETDRS method following refraction;
complete ophthalmic examination including slit-lamp biomicroscopy, indirect ophthalmoscopy and TOP;
Heidelberg OCT imaging:
dilated color fundus photography;
Heidelberg fluorescein angiography; and
perform assigned intravitreal injection.

Week 1 Visit included queries for adverse events, medication changes and medical procedures. The following procedures were performed:
standard BCVA, using ETDRS method following refraction;
complete ophthalmic examination including slit-lamp biomicroscopy, indirect ophthalmoscopy and TOP;
Heidelberg OCT imaging; and
perform assigned intravitreal injection or sham.

Weeks 4, 8, 12, 16, 20, 24, 28 and 32 Visits included queries for adverse events, medication changes and medical procedures. The following procedures were performed:
standard BCVA, using ETDRS method following refraction;
complete ophthalmic examination including slit-lamp biomicroscopy, indirect ophthalmoscopy and TOP;
Heidelberg OCT imaging; and
perform assigned intravitreal injection per protocol (or sham).

Week 36 (exit) Visit included queries for adverse events, medication changes and medical procedures. The following procedures were performed:
standard BCVA, using ETDRS method following refraction;
complete ophthalmic examination including slit-lamp biomicroscopy, indirect ophthalmoscopy and TOP;
Heidelberg OCT imaging;
dilated color fundus photography; and
Heidelberg fluorescein angiography.

The primary efficacy endpoint included:
change in edema from baseline to week 36 as measured by CST on Heidelberg OCT.

The secondary efficacy endpoints included:
change in BCVA from baseline to week 36; and
change in intraretinal and subretinal edema from baseline to week 36;
change in CNV lesion components: subretinal retinal hyper-reflective material, pigment epithelial detachment thickness; and
number of injections required to control choroidal neovascularization based on volume of subretinal fluid.

Data Analysis. The analysis of data from the study is performed when all subjects have either completed the visit at week 6 or discontinued early from the study. Both univariate and multivariate analyses are done.

TABLE 2-2

Study Patient Demographics

| Characteristic | Combo(SRL + EYL) | Monotherapy EYL) |
|---|---|---|
| sex | 4 male + 6 female | 2 male + 8 female |
| average age | 71 | 77 |
| average duration of exudative AMD (months) | 64 | 68 |
| average pre-study anti-VEGF Tx | 43 | 34 |
| average time since last IVT Tx (weeks) | 4.8 | 6.3 |
| baseline BCVA | 62.6 | 61.0 |
| baseline OCT CST | 393 | 446 |

Figure 5:
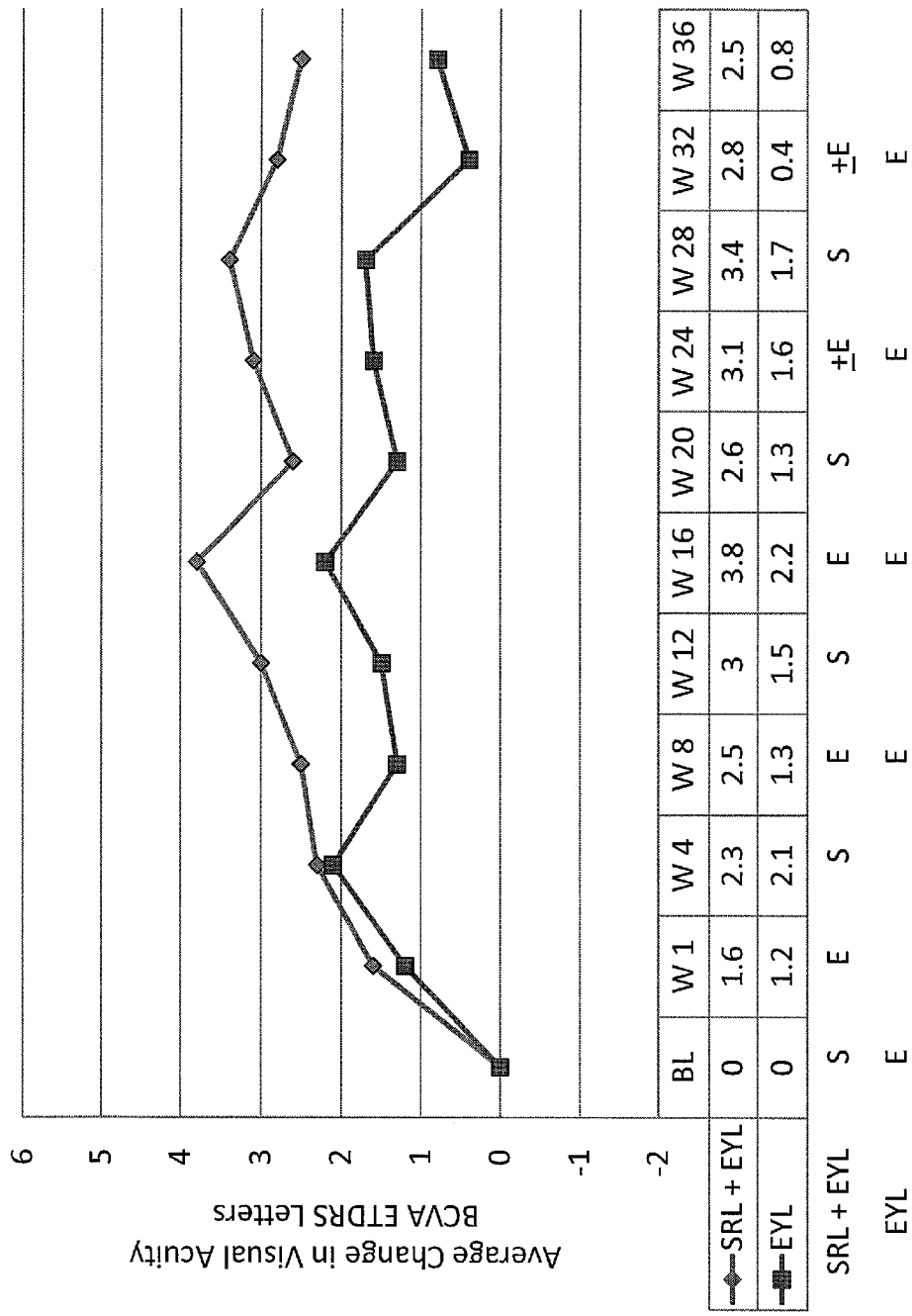
FIG. 5 shows the average change in visual acuity in subjects of the combination (sirolimus+anti-VEGF) and monotherapy (anti-VEGF alone) treatment groups as determined by measuring best corrected visual acuity (BCVA) as part of the study of Example 2.
Figure 6:
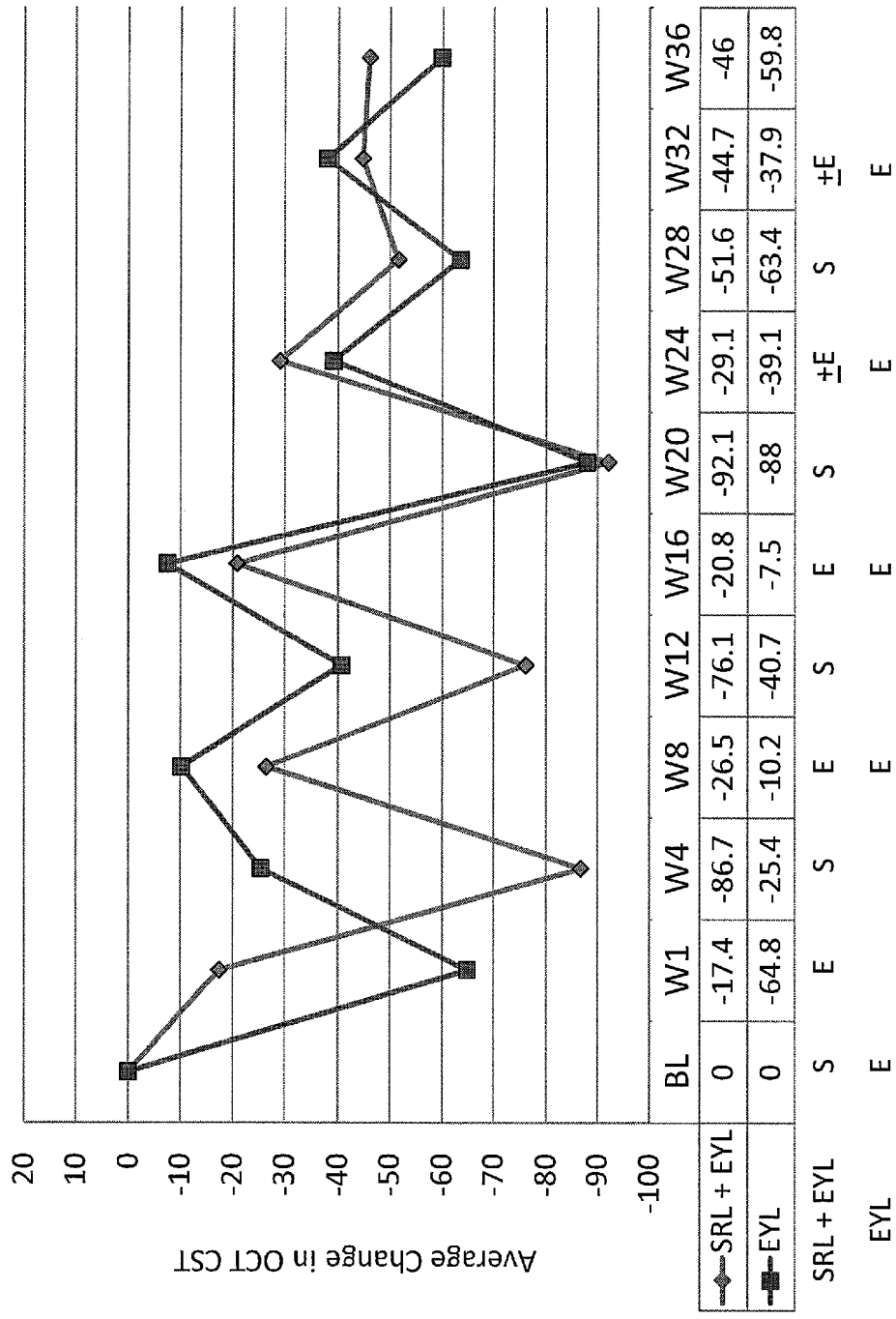
FIG. 6 shows the average change in central subfield thickness (CST) in subjects of the combination (sirolimus+anti-VEGF) and monotherapy (anti-VEGF alone) treatment groups as determined by optical coherence tomography (OCT) as part of the study of Example 2.

Results. Two of ten patients in the combo group received sham injections at week 24, and four of ten patients in the combo group received sham injections at week 32. Thus administration of SRL reduced the need for anti-VEGF treatment to control edema associated with exudative AMD in 40% of the subjects in the combination group Additionally, as shown in FIG. 5, visual acuity improved in the combination group (+2.5 letters) to a greater extent than in the monotherapy group (+0.8 letters). Moreover, as shown in FIG. 6, a considerably greater reduction in edema was observed in the combination group at weeks 4 and 12 as compared to the monotherapy group. However, the reduction in edema observed in the combination group at the later time points did not differ remarkably from the reduction observed in the monotherapy group. One of the ten patients in the monotherapy group had a very high baseline OCT CST value (646 microns), which amounted to the best potential for improvement among the 20 study subjects. This outlier in the monotherapy group and the decision to defer EYL injections at weeks 24 and 32 in the combination group is thought to contribute to the lack of superiority of the combination group throughout the course of the study and particularly in the later weeks.

The invention claimed is:

1. A method of treating persistent intraretinal or subretinal edema due to exudative AMD despite previous intravitreal anti-VEGF treatment in a human subject, the method comprising:
    administering an effective amount of a liquid formulation to the human subject by intravitreal injection to treat persistent intraretinal or subretinal edema, wherein
    the liquid formulation comprises from about 1% (w/w) to about 10% sirolimus or a pharmaceutically acceptable salt thereof.

2. The method of claim 1, wherein the effective amount of the liquid formulation comprises from 200 to 900 μg sirolimus.

3. The method of claim 1, wherein the previous intravitreal anti-VEGF treatment comprises at least three previous injections in the past three to seven months.

4. The method of claim 3, wherein the anti-VEGF treatment comprises treatment with an anti-VEGF monoclonal antibody or VEGF-binding fragment thereof.

5. The method of claim 4, wherein the anti-VEGF monoclonal antibody is a human antibody or a humanized antibody.

6. The method of claim 3, wherein the anti-VEGF treatment comprises bevacizumab, ranibizumab, aflibercept or pegaptanib.

7. The method of claim 1, wherein the treatment of persistent intraretinal or subretinal edema achieves a decrease in edema in a treated eye of at least about −15 microns in central subfield thickness as measured by optical coherence tomography about one month (±week) after administration of the liquid formulation.

8. The method of claim 1, wherein the administering is done once every two months for at least two months and the treatment of persistent intraretinal or subretinal edema achieves a decrease in edema in a treated eye of at least about −30 microns in central subfield thickness as measured by optical coherence tomography about one month (±week) after a second administration of the liquid formulation.

9. The method of claim 1, wherein the administering is done once every two months for at least four months and the treatment of persistent intraretinal or subretinal edema achieves a decrease in edema in a treated eye of at least about −40 microns in central subfield thickness as measured by optical coherence tomography about one month (±week) after a third administration of the liquid formulation.

10. The method of claim 1, wherein the liquid formulation comprises about 2% (w/w) sirolimus or a pharmaceutically acceptable salt thereof, about 94% (w/w) polyethylene glycol 400, and about 4% (w/w) ethanol and the effective amount of the liquid formulation comprises about 440 μg sirolimus.

11. The method of claim 1, wherein the method further comprises:
    administering an effective amount of an anti-VEGF agent to the human subject by intravitreal injection to treat the exudative AMD, wherein
    the anti-VEGF agent is administered at from one to five weeks after administration of the liquid formulation.

12. The method of claim 1, wherein the method further comprises:
    administering an effective amount of an anti-VEGF agent to the human subject by intravitreal injection to treat the exudative AMD, wherein
    both the liquid formulation and the anti-VEGF agent are administered at least twice,
    the anti-VEGF agent is administered every seven to nine weeks, and
    the liquid formulation is administered every three to five weeks after administration of the anti-VEGF agent.

13. The method of claim 12, wherein both the liquid formulation and the anti-VEGF agent are administered at least three times.

* * * * *